US007647285B2

(12) United States Patent
Heckerman et al.

(10) Patent No.: US 7,647,285 B2
(45) Date of Patent: Jan. 12, 2010

(54) TOOLS FOR HEALTH AND WELLNESS

(75) Inventors: David E. Heckerman, Bellevue, WA (US); Craig J. Mundie, Redmond, WA (US); Nebojsa Jojic, Redmond, WA (US); Randy J. Hinrichs, Sammamish, WA (US)

(73) Assignee: Microsoft Corporation, Redmond, WA (US)

( * ) Notice: Subject to any disclaimer, the term of this patent is extended or adjusted under 35 U.S.C. 154(b) by 520 days.

(21) Appl. No.: 11/556,085

(22) Filed: Nov. 2, 2006

(65) Prior Publication Data

US 2007/0112598 A1 May 17, 2007

Related U.S. Application Data

(63) Continuation-in-part of application No. 11/266,974, filed on Nov. 4, 2005, now Pat. No. 7,406,453.

(51) Int. Cl.
*G06E 1/00* (2006.01)
*G06E 3/00* (2006.01)
*G06F 15/18* (2006.01)
*G06G 7/00* (2006.01)

(52) U.S. Cl. ........................................ 706/20; 706/62

(58) Field of Classification Search .................... 706/20
See application file for complete search history.

(56) References Cited

U.S. PATENT DOCUMENTS

| 6,311,163 | B1 | 10/2001 | Sheehan et al. |
| 6,564,207 | B1 | 5/2003 | Abdoh |
| 6,669,631 | B2 | 12/2003 | Norris et al. |
| 6,789,091 | B2 | 9/2004 | Gogolak |
| 6,820,070 | B2 | 11/2004 | Goldman et al. |
| 6,920,448 | B2 | 7/2005 | Kincaid et al. |
| 6,945,458 | B1 | 9/2005 | Shah et al. |
| 6,947,933 | B2 | 9/2005 | Smolsky |
| 7,009,511 | B2 * | 3/2006 | Mazar et al. ................. 340/531 |
| 7,065,409 | B2 * | 6/2006 | Mazar ......................... 607/60 |

(Continued)

FOREIGN PATENT DOCUMENTS

KR   1020030062728 A   7/2003

(Continued)

OTHER PUBLICATIONS

Using of local information for diagnosing intranatal adverse conditions by pulse oximetry Guler, N.; Gurgen, F.; Arikan, G.; Engineering in Medicine and Biology Society, 2001. Proceedings of the 23rd Annual International Conference of the IEEE vol. 4, Oct. 25-28, 2001 pp. 3710-3713 vol. 4.*

(Continued)

*Primary Examiner*—Michael B Holmes
(74) *Attorney, Agent, or Firm*—Lee & Hayes, PLLC

(57) ABSTRACT

A tool for providing health and/or wellness services is described herein. Not necessarily clean or unclean data about a plurality of self-selected or non-selected or unselected subjects is received. The data can be aggregated and mined at least in part by employing a statistical algorithm, a data-mining algorithm and/or a machine-learning algorithm. The data can be further employed to provide health and/or wellness services to participants.

14 Claims, 17 Drawing Sheets

U.S. PATENT DOCUMENTS

| | | | | | |
|---|---|---|---|---|---|
| 7,127,300 | B2 * | 10/2006 | Mazar et al. | ............... | 607/60 |
| 7,289,761 | B2 * | 10/2007 | Mazer | ............... | 455/1 |
| 7,292,139 | B2 * | 11/2007 | Mazar et al. | ............... | 340/531 |
| 7,395,117 | B2 * | 7/2008 | Mazar et al. | ............... | 607/60 |
| 2003/0225597 | A1 | 12/2003 | Levine | | |
| 2004/0172297 | A1 * | 9/2004 | Rao et al. | ............... | 705/2 |
| 2005/0234740 | A1 | 10/2005 | Krishnan et al. | | |

FOREIGN PATENT DOCUMENTS

| | | |
|---|---|---|
| KR | 1020050085778 A | 8/2005 |
| KR | 1020050113848 A | 12/2005 |

OTHER PUBLICATIONS

Prognostic value of heart rate variability analysis in patients with depressed left ventricular function irrespective of cardiac rhythm Sosonowski, M.; Macfarlane, P.W.; Parma, R.; Skrzypek-Wanha, J.; Tendera, M.; Computers in Cardiology, 2006 Sep. 17-20, 2006 pp. 81-84.*

Validation of a novel algorithm for ventricular repolarization analysis: use of Physionet resources Cantini, F.; Emdin, M.; Passino, C.; Varanini, M.; Conforti, F.; Computers in Cardiology, 2003 Sep. 21-24, 2003 pp. 509-512 Digital Object Identifier 10.1109/CIC.2003.1291204.*

European search report dated Jan. 16, 2008, international application No. PCT/US2007/082052, 3 pages.

* cited by examiner

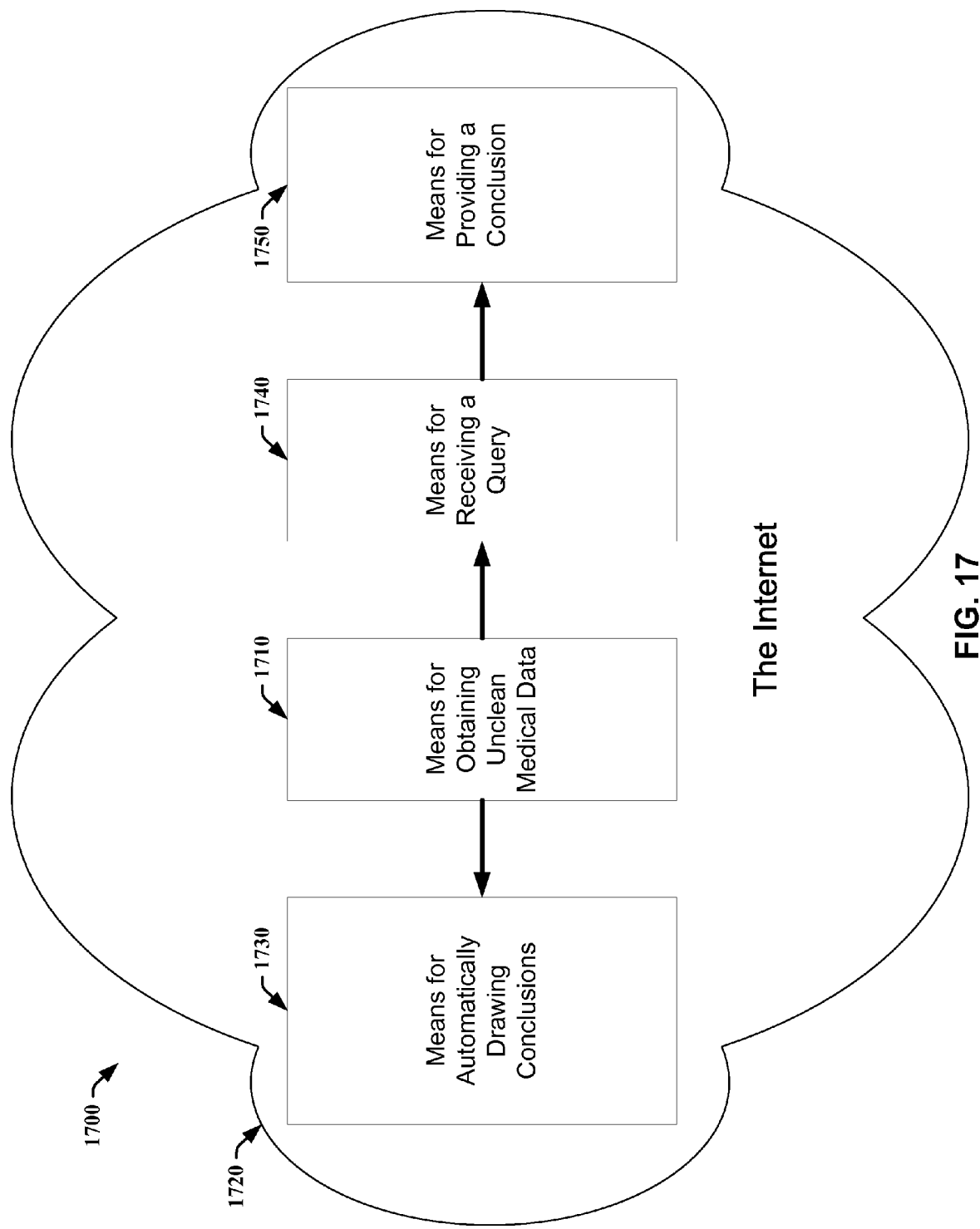

TOOLS FOR HEALTH AND WELLNESS

CROSS-REFERENCE TO RELATED APPLICATIONS

This application is a Continuation-in Part of U.S. patent application Ser. No. 11/266,974, entitled "LARGE-SCALE INFORMATION COLLECTION AND MINING," filed Nov. 4, 2005. This application is also related to U.S. patent application Ser. No. 11/556,069, entitled, "MONETIZING LARGE-SCALE INFORMATION COLLECTION AND MINING", filed Nov. 2, 2006. The entireties of the aforementioned applications are incorporated herein by reference.

BACKGROUND

Many industries benefit from drawing statistically-valid conclusions from data. For instance, health-care providers increasingly base diagnostic and treatment decisions as well as wellness recommendations on the current best evidence (i.e., increasingly they practice evidence-based medicine). Preferably, clinicians rely on the "gold standard" of evidence when making medical decisions—randomized, controlled, double-blind clinical trials. If clean data from a randomized, controlled, double-blind clinical trial relating to a patient's condition is not available, clinicians often rely on other sources of clean data that best adhere to the well-established principles of the scientific method. Examples of clean data include randomized, controlled, double-blind clinical trials, controlled but not randomized clinical trials, uncontrolled clinical trials, unblinded clinical trials, and other types of studies involving researcher selected populations. However, clean data is expensive and time-consuming to obtain and, depending on the patient's condition, may not be available at all.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Although it is desirable to draw conclusions from clean data, collecting clean data is complex, time-consuming and costly to perform. Since a larger sample size helps to overcome the effects that a lack of a selected population and/or a lack of controls have on statistical significance, analyzing large amounts of unclean or not necessarily clean data (e.g., data from a non-selected, unselected or self-selected population) can yield valuable information. Unclean data can be of any type including but not limited to health-related information. The data can be provided explicitly or automatically culled from existing information (e.g., frequency of prescription refills as an indication of whether a patient is taking their medication as prescribed). Although data so obtained may be noisy, machine-learning/data-mining algorithms can be used to "see" through this noise to discover useful patterns. The mining process can be directed toward, for example, elucidating new drug side effects and/or interactions among drugs and/or diseases.

The unclean database also can be used, for instance, to provide those individuals contributing to the database with information and/or services. By way of example, the database can facilitate providing services such as self-diagnosis (e.g., health and wellness, etc.), self treatment advice and/or guidance regarding seeking and identifying professional assistance (e.g., referrals, facilitating medical appointments, etc.). The guidance can be based on a variety of factors, such as the complexity of the diagnosis/problem/condition, the nature of the diagnosis/problem/condition, the location of the individual and/or the budget of the individual. In order to protect an individual's privacy, information about an individual can be stored anonymously, for instance by associating a subscriber number with a user password or by employing any other mechanism to protect confidential information. Additionally or alternatively, a user can be asked to consent to the dissemination of the user's information to third parties.

Moreover, the database can facilitate personalizing healthcare. For instance, as the cost of gene sequencing drops, it is expected that people routinely will have their genes sequenced. This patient-specific genetic data can be correlated with an individual's health history and/or health-related behaviors to, for example, identify personalized diagnostic procedures and personalized therapies for medical conditions.

The following description and the annexed drawings set forth in detail certain illustrative aspects of the subject matter. These aspects are indicative, however, of but a few of the various ways in which the subject matter can be employed and the claimed subject matter is intended to include all such aspects and their equivalents.

BRIEF DESCRIPTION OF THE DRAWINGS

FIG. 17 is a block diagram representing one example of an online system to facilitate providing health and/or wellness assistance.

DETAILED DESCRIPTION

Figure 1:
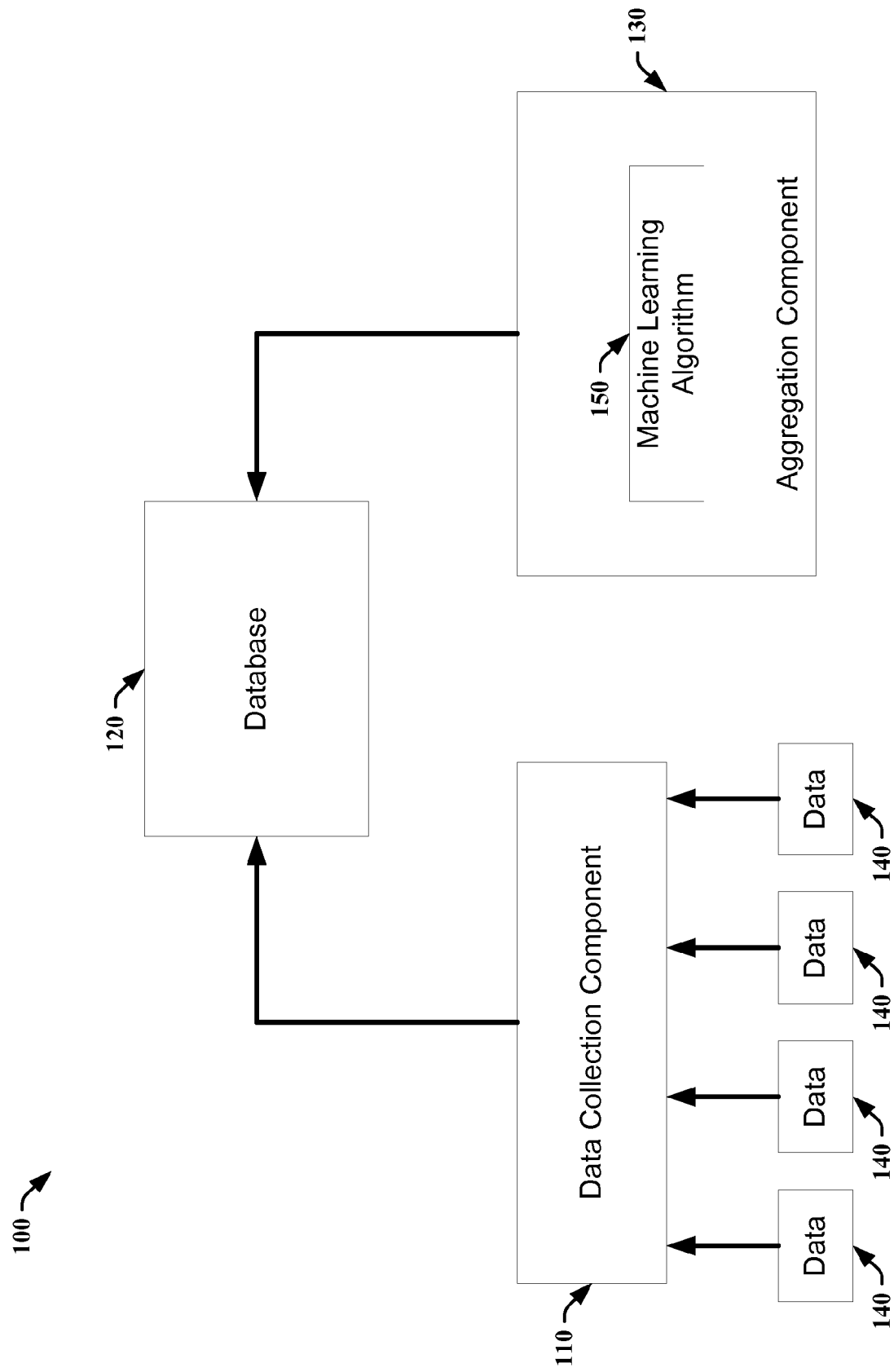
FIG. 1 is a block diagram of one example of a system that facilitates health-information reporting.

The subject matter described herein facilitates collecting and mining very large amounts of unclean or not necessarily clean data and optionally storing the information in a database. Because the collected data can be associated with a particular user, a useful by-product of the data collection process is the facilitation of providing health and/or wellness advice/services to a user. By way of example, a user can open an interactive session with a tool for accessing the database. The tool can provide an interface with the database via text, audio and/or video. For instance, a dialog can be started with the user that leads the user through a series of questions to facilitate converging on an accurate diagnosis, treatment option or referral. The interface can optionally receive real-time data (manually input and/or by sensors) such as temperature, location, weight, facial expression, etc. Upon reaching a conclusion having a predetermined level of confidence, the tool can provide the user with a diagnosis, including background information on the diagnosis, and/or treatment options and health-care referrals. Emergency medical teams can use portable versions of the tool to enter patient information at the site of the emergency in order to have a preliminary diagnosis sent to the emergency room (ER) prior to a patient's arrival at the ER or to inform emergency personnel of available interventions.

The data input can be of any type including but not limited to health-related information. In one embodiment, health-related information can be obtained from a wide variety of sources including but not limited to directly from patients via a computerized service, such as a web site using a web form for entering information. The data can be correlated with information from a variety of different sources and/or systems to facilitate drawing conclusions relating to the patient's health. Any source having pertinent information can subscribe to the web service to provide information. Such sources of information include insurers, providers (e.g., doctors, nurses, hospitals, nursing homes, etc.) and devices (e.g., pacemakers, smart scale, etc.).

To encourage user participation, incentives can be provided and/or the data can be anonymized to address patient privacy concerns. For example, a third-party payer can require a subscriber to file a report as a condition of renewing a prescription for medication or to qualify for a lower co-payment/rate. In another embodiment, coupons for discounts on goods and/or services can be offered. With regard to anonymity, for example, no identifying information may be required (such as name and address) and instead an anonymous ID (e.g., passport ID) can be assigned to a user. An anonymous ID allows for separate health reports from the same individual to be linked together without associating identifying information with the data.

Another way to encourage participation is through minimizing the effort needed for a user to interact with the system. For instance, a free-text entry system with intelligent spelling correction can be provided for data entry. Text mining algorithms can be employed to extract structured data from the entered free-text. In another embodiment, a bar-code reader can be used to scan the label of a medication bottle.

By way of another example, at the time of each report, the user can be asked health-related questions. The questions can be selected at random from a large library of questions or more particularly tailored to the user's condition/context. Data can be entered at will (e.g., symptoms such as chest pains, level of arthritis pain, etc.) and/or the user can request that reminders be sent (e.g., periodic email, etc.). The individual data can be aggregated (e.g., collected en masse or selected based on the type of data to be analyzed or otherwise refined) in whole or in part across a large group and patterns/correlations can be discovered from the data using, for example, statistical methods. Any suitable statistical method can be used, such as Fisher's Exact Test (if both variables are binary), Mann-Whitney (if one variable is binary and the other is a number), and Spearman correlation (if both variables are numbers).

By way of yet another example, users can be presented with questions based on the results of previously analyzed data. For instance, statistical methods can be used to analyze data input by users who happen to report or who are prompted to report side effects while taking medications. In this example, if a correlation between Drug A and a side effect and a correlation between Drug B and the same side effect are detected and rise above a threshold, subsequent users can be presented with questions about Drug A, Drug B and the side effect. In particular, if any person input information about Drug A, Drug B or the side effect spontaneously, he or she could be asked about the other two. Alternatively or additionally, other users could be chosen at random to be asked about all three. Data input by users who answered questions pertaining to all three (e.g., a stratified sample) can be subjected to standard multivariate tests (e.g., a logistic regression of Drug A and Drug B on the side effect) to determine, for instance, if the two drugs interact to produce the side effect. Based on the results of the analysis, appropriate response(s) can be implemented (e.g., if a user reports he/she is taking Drug A, the user can be asked about Drug B and be advised about the likely side effect if taking both).

The interface can be programmed to maximize the value of information while minimizing the effort required to provide the information. For example, questions can be selected automatically in a manner so as to converge on meaningful information and to otherwise maximize the value of the extracted information in conjunction with the already mined data. One way to accomplish this is to increase the number of patients being asked the same questions when the answers to randomized questions start showing a distinct but weak pattern in order to confirm the pattern. The patterns in free text may suggest an effect that needs further exploration with new questions, for instance, questions that were previously found to be informative when asked in conjunction with the observed pattern.

Another way to increase usage is to increase awareness of the service. By way of example, health-related keywords can be purchased on a search site (e.g. MSN SEARCH). When a user types a query containing one of the purchased keywords, the user is presented with a link to a web site enabling data collection. Other advertising venues can be employed (e.g. print, radio, TV, etc) and these ads can contain catchy phrases to describe the process of filing a report (e.g., encourage people to send in their "drug bugs").

The collected data can be utilized to generate revenue. For instance, the conclusions, discovered knowledge and/or the raw data can be forwarded to health-related agencies and/or private companies (e.g., pharmaceutical, biotechnology, medical device, etc.) or these entities can be otherwise given access to the data (e.g., an interface to access the database) for a fee. By way of example, the fee can be applied on a per use basis or a subscription service can be provided (e.g., payment for unlimited or limited access to the database for a period of time).

FIG. 1 schematically illustrates one example of a system 100 that facilitates large-scale reporting of health-related data. The term large-scale is used herein to mean large enough to produce the desired results (e.g., large enough to facilitate discerning one or more patterns from health information related to a non-selected population). The system 100 comprises a data collection component 110, a database 120 and an aggregation component 130. The data collection component 110 collects data 140 on a large-scale from a non-selected population and provides the data 140 to the database 120. The term non-selected is used herein to differentiate from studies on selected populations such as conventional clinical trials (which enroll subjects according to enrollment criteria) and public health studies (which focus on particular groups within the population). The aggregation component 130 applies a machine-learning algorithm 150 to the database 120 to discern patterns in the data 140. The data collection component 110 and aggregation component 130 can be the same process executing on a single or a plurality of computers or multiple processes executing on a single or a plurality of computers. Similarly, the database 120 can be a single datastore or multiple datastores. Moreover, the components 310, 330 and the database 320 can be implemented by software or combinations of software and hardware.

The data collection component 110 can collect any type of data 140 including but not limited to biological, pathophysiological, physiological, medical, healthcare and/or otherwise health-related. The data 140 can be, for example, a drug-related event, a symptom, and/or genetic information. The data collection component 110 can collect data 140 in any form including but not limited to textual, graphical, photographic, sound, speech, video, multimedia and the like. By way of example, the data collection component 110 can allow for free-text analysis. In this embodiment, rather than prompting a user with forms, a user enters the data in free-text form and the system automatically extracts and structures data from the free-text. The free-text analysis can include intelligent spelling correction or voice recognition. The user can be a consumer or a provider of healthcare services or any other source of health-related information. The data component 110 also can allow for input to be received in multiple forms in combination, such as both free-text and survey forms. The data 140 even can be introduced in the form of an activity, such as a memory game that a user plays to assess memory function.

The data collection component 110 can automatically obtain data 140, such as by querying a provider database (not shown). The data 140 can be provided to the data collection component 110 from any input means, such as a PDA, telephone, bar code reader, computer, keyboard, mouse, microphone, touchscreen, database, cell phone, etc. To promote participation through convenience of use, sites for data entry, such as kiosks with computer terminals, can be provided at public and other locations.

In one embodiment, the data collection component 110 can collect the data 140 anonymously such that no identifying information is linked to the data 140. By way of example, a user can be anonymously issued an ID, and use this ID to log on to the system 100 to enter data 140. The data from a particular individual can be linked together via this ID without associating the user's identity with the data. Alternatively, the data can be received by the data collection component 110 in conjunction with identifying information, and the data collection component 110 can filter the identifying information (privacy filter) prior to storage in the database 120. In addition, the data collection component 110 can employ various security measures to obtain data 140, such as a Human Interactive Proof (HIP) to verify that a human being (rather than an automated process) is providing the data 140.

The data 140 in whole or in part is sent to the database 120 to be stored for use by the aggregation component 130. The aggregation component 130 aggregates individual data across a large group and facilitates automatically detecting one or more patterns from the data 140 at least in part by utilizing machine-learning techniques 150 to mine the database 120. The term pattern as used herein includes but is not limited to trends, associations, correlations, connections, links, relationships, etc. By way of example, the aggregation component 130 can detect a correlation between the use of a certain medication and, for instance, a symptom across a large group of people. The aggregation component 130 can be structured to accord different weights to different data. For instance, data from a physician can be given a higher weight than data from a patient. By way of another example, data more likely to be accurate can be assigned a greater weight. Moreover, the aggregation component 130 can classify the data 140 according to demographics (e.g., age, gender, race, etc.) in order to facilitate recognizing demographic-specific patterns.

The patterns (e.g., correlations) can be ascertained via any suitable method, for example, by employing an algorithm 150 such as the statistical methods explained above (Fisher's Exact Test, Mann-Whitney, Spearman correlation). Additionally or alternatively, the system 100 can employ an algorithm 150 that uses low-order sufficient statistics and statistical methods that can make inferences with missing data (e.g., expectation-maximization (EM) algorithm). Any machine-learning algorithm 150 can be employed, such as neural networks, expert systems, Bayesian belief networks, fuzzy logic, data fusion engines and the like. The aggregation component 130 also can employ combinations of various artificial intelligence techniques to discern patterns.

Optionally, a human intervention step can be combined with the machine-learning algorithm 150 to discern patterns from the data 140. By way of example, a human editor can inspect and even test (e.g., through formal or informal clinical trials) some or all of the patterns ascertained by the automated portion 150 of the system 100 before the system 100 accepts a pattern as true or likely to be true.

In one embodiment, the data collection component 110 and the aggregation component 130 can function together to collect and aggregate the data, such as by tailoring questions to converge on the most valued information. By way of example, the data collection component 110 can present a user with a question and the aggregation component 130 can apply machine-learning techniques 150 to the answer to determine a suitable follow-up question. A suitable follow-up question can be based on the user's response and/or patterns detected from the responses given by other users to the same or a similar question, for instance, to confirm a pattern. By way of example, a user can be presented with the question "How are you feeling today?" If the user's response is "I do not feel well today," the aggregation component 130 can choose the follow-up question "Please tell me about your symptoms." If the user responds "I have chest pain" and the system 100 has acquired data 140 from other users taking a particular type of medication that shows a pattern of chest pain associated with that particular medication, the system 100 can respond by asking the user "Please tell me what medications you are taking." By way of another example, a physician can be queried about the number of patients he/she has treated who are on a particular medication and who have experienced symptoms, such as chest pain. Moreover, questions can be tailored to the personal characteristics of the user, such as education level, language, culture and dialect.

In another embodiment, the system 100 can facilitate the design of personalized diagnostic and therapeutic regimens as well as alert/remind a user about behavior modifications that would benefit the user's health. By way of example, the data collection component 110 can obtain patient-specific genetic information as well as a variety of other relevant information from a user and/or provider and/or device, etc. The machine-learning component 150 can correlate the patient-specific genetic information with the other relevant information to draw conclusions about a user's health needs. For instance, if the patient-specific genetic information indicates that the person has a genetic susceptibility to heart disease and other relevant information indicates that the person smokes cigarettes and/or eats a high-fat diet and/or has a high cholesterol, the user can be sent an alert notifying him/her of various beneficial behavioral modifications that could reduce his/her risk of a heart attack (e.g., quitting smoking, reducing dietary fat, etc.) as well as advantageous medical therapies (e.g., cholesterol lowering drugs). By way of another example, if the patient-specific genetic information indicates the person is at high risk for a certain type of cancer, the person can be sent a reminder/alert to discuss with their physician various preventative therapies as well as useful diagnostic tests.

Figure 2:
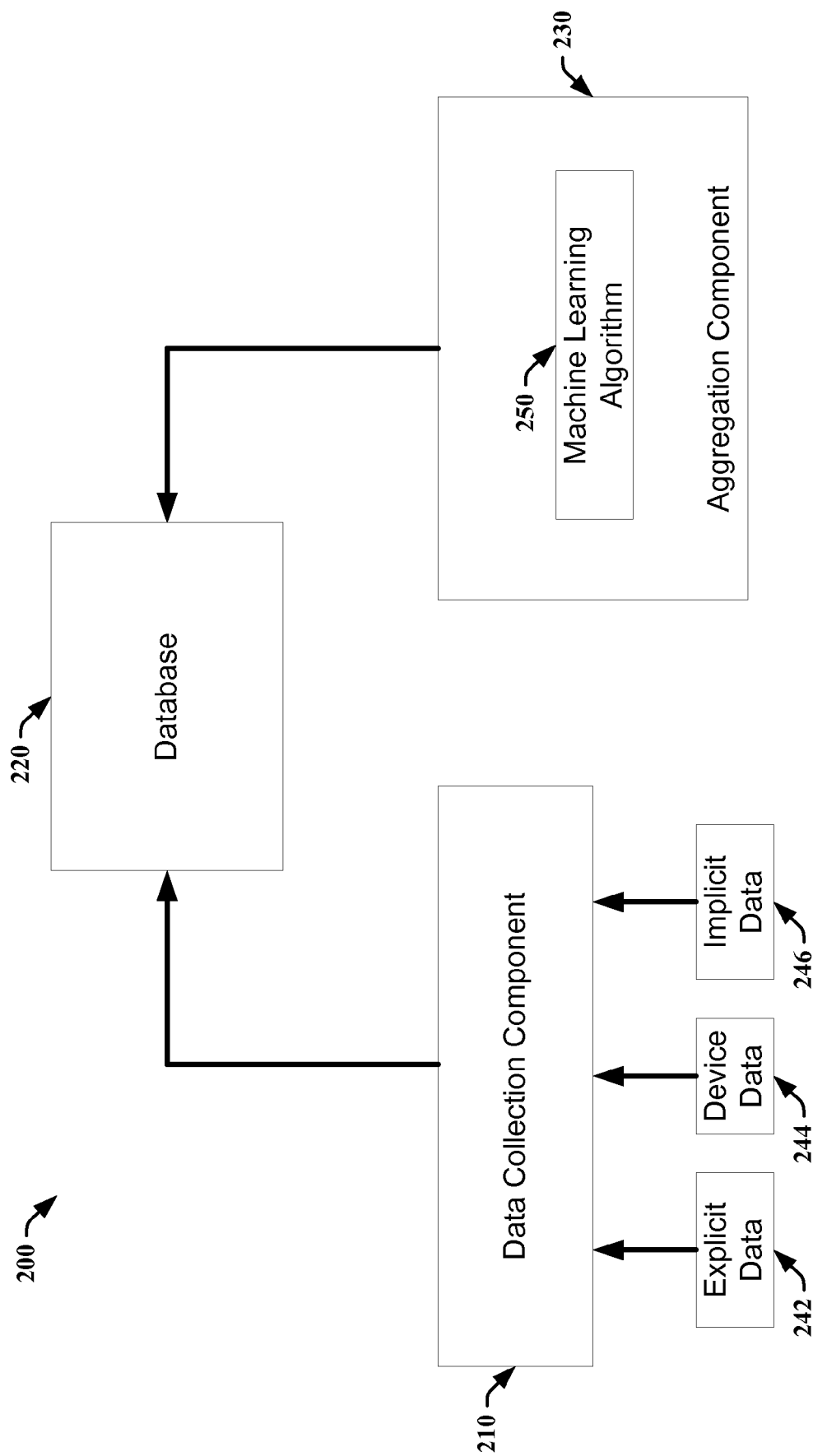
FIG. 2 is a block diagram of another example of a system that facilitates health-information reporting.

FIG. 2 schematically illustrates another example of a system 200 that facilitates large-scale reporting of health-related data. The system 200 comprises a data collection component 210, a database 220 and an aggregation component 230. The data collection component 210 can collect data 242-246 from a variety of different sources on a large-scale relating to a non-selected population and provides the data 240-260 in whole or in part to the database 220. The aggregation component 230 applies a machine-learning algorithm 250 to the database 220 to facilitate drawing conclusions from the data 242-246. The data collection component 210 and aggregation component 230 can be the same process executing on a single or a plurality of computers or multiple processes executing on a single or a plurality of computers. Similarly, the database 120 can be a single datastore or multiple datastores. Moreover, the components 210, 230 and the database 220 can be implemented by software or combinations of software and hardware.

As explained in relation to FIG. 1, a variety of different input means can be employed to provide the data 242-246. Data 242-246 can be received in a variety of different forms, such as explicit data 242 and/or implicit data 246. By way of example, explicit data 242 can be data directly entered by a patient or a provider (e.g., physician, nurse, pharmacy, hospital, institution, agency, device data 244, etc.).

In order to encourage participation, the data collection component 210 can automate the data collection process in whole or in part. For instance, the data collection component 210 can acquire implicit data 246. Implicit data 246 as used herein means data that is a by-product of the activities that people engage in and/or information that is provided to the system 200. By way of example, implicit data 246 can be acquired from explicit data 242. For instance, a user can be asked a broad question by the system 200, such as "How are you feeling?" The user can enter his/her answer in free-text form and the system 200 can interpret this answer to extract implicit data 246. If the user's answer is "I am not feeling well and my eyes are red and itchy and I am sneezing quite a bit," the system 200 can determine that the user has allergies. By way of another example, the data collection component 210 can automatically acquire a user's prescription medication history by querying a pharmacy database (not shown). By analyzing the user's refill history, the system 200 can determine whether the user is taking the medication as prescribed. The system 200 can employ various techniques and methodologies to gather the implicit data 246, such as a machine-learning algorithm 250.

The data collection component 210 also can receive device data 244. The data collection component 210 can interrogate devices to obtain the device data 244 and/or the devices can initiate data transfers. Any form of communication between the system 200 and the devices can be employed, such as direct connection, wireless connection, network connection, etc. By way of example, device data 244 can be data received from a smart scale that can automatically connect with the system 200 to send a patient's weight. Other devices that can send device data 244 include pacemakers, defibrillators, thermometers, consumer healthcare devices, electronic calendars, PDAs, cell phones, exercise equipment, and the like. For instance, a user can keep track of how often they have a particular symptom by entering this information into his/her electronic calendar. This information can be uploaded to the data collection component 210 by the electronic calendar, for instance, upon receiving a reminder, by user indication, and/or automatically without receiving a prompt. Alternatively, the system 200 can interrogate the electronic calendar. By way of another example, the devices can connect with the system 200 by using a platform such as MICROSOFT .NET.

Figure 3:
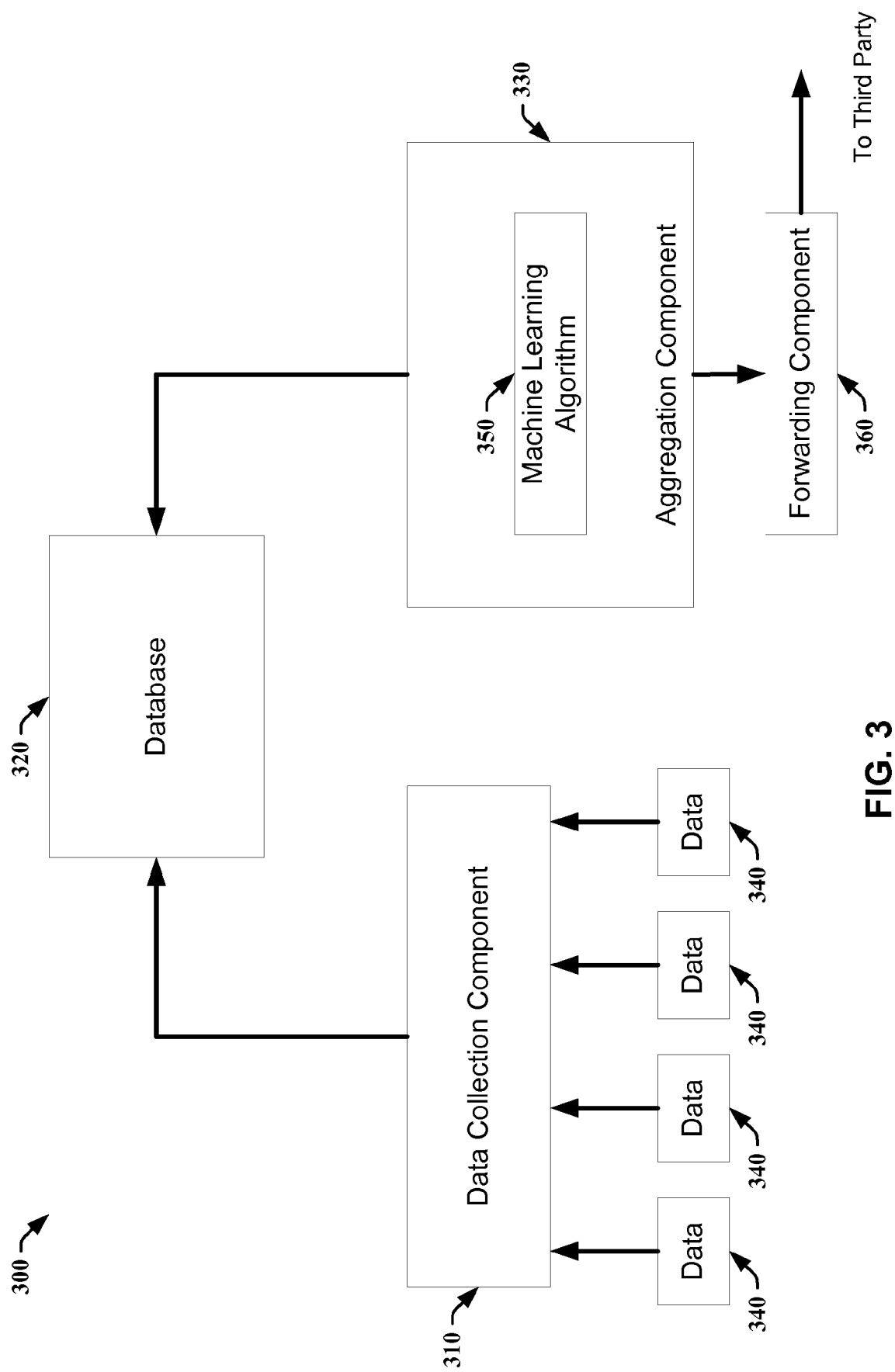
FIG. 3 is a block diagram of another example of a system that facilitates health-information reporting.

FIG. 3 schematically illustrates another example of a system 300 that facilitates large-scale reporting of health-related data. The system 300 comprises a data collection component 310, a database 320, an aggregation component 330 and a forwarding component 360. The data collection component 310 collects data 340 on a large-scale relating to a non-selected population and provides the data 340 in whole or in part to the database 320. The aggregation component 330 applies a machine-learning algorithm 350 to the database 320 to discern patterns in the data 340. The forwarding component 360 forwards at least one pattern to a third party. The forwarding component 360 can forward information in any form, including but not limited to a data signal, online transmission, wirelessly, email, telephone, facsimile, blackberry, cell phone, etc.

The components 310, 330 and 360 can be the same process executing on a single or a plurality of computers or multiple processes executing on a single or a plurality of computers. Similarly, the database 320 can be a single datastore or multiple datastores. Moreover, the components 310, 330 and 360 and the database 320 can be implemented by software or combinations of software and hardware.

The third party that receives the patterns from the system 300 can be a patient, a provider (e.g., physicians, hospitals, pharmacies, nursing homes, etc.), a governmental entity (e.g., Food & Drug Administration (FDA), lawmakers, etc.), a private entity (e.g., pharmaceutical companies, medical device companies, distributors, drug safety watchdog groups, insurance companies, AARP, etc.) and any other interested parties. By way of example, by mining the database 320 for associations between adverse events and medications, the system 300 can facilitate the early detection of drug side effects and/or drug interactions. The system 300 can forward this information to alert interested parties, such as the company that manufactures the medication(s) associated with the adverse event and/or the FDA. By way of another example, a user can register with the system 300 and sign-up for alerts relating to a medication the user is taking. If a pattern associated with the user's medication is recognized by the system 300, the forwarding component 360 can send an alert to the user notifying the user of the relationship.

The system 300 also can facilitate the detection of counterfeit drugs. By way of example, the data collection component 310 can collect information relating to a user's medication and physiological status and correlate this information to determine if the medication is producing the intended effect.

In one embodiment, the user can be queried about medications and the specific effects of those medications. Alternatively, a device can provide an output corresponding to a measure of the patient's response to the therapy. For instance, if a patient is taking blood pressure medication, the patient can enter the medication's name as well as the patient's blood pressure measurements via the data collection component 310. The system 300 can store this information over time and determine if the patient is adequately responding to the therapy, for instance, by employing machine-learning techniques 350. If the system 300 determines that the patient's response to the medication is inadequate, the forwarding component 360 can send the patient an alert.

The system 300 can forward the patterns to the interested parties in return for a fee. The fee can be structured in any manner, for instance, a fee can be charged for each alert sent to the third party. Alternatively, a subscription service can be provided such that a third party is charged a fee for unlimited or limited access to information inferred by the system 300 for a period of time.

Figure 4:
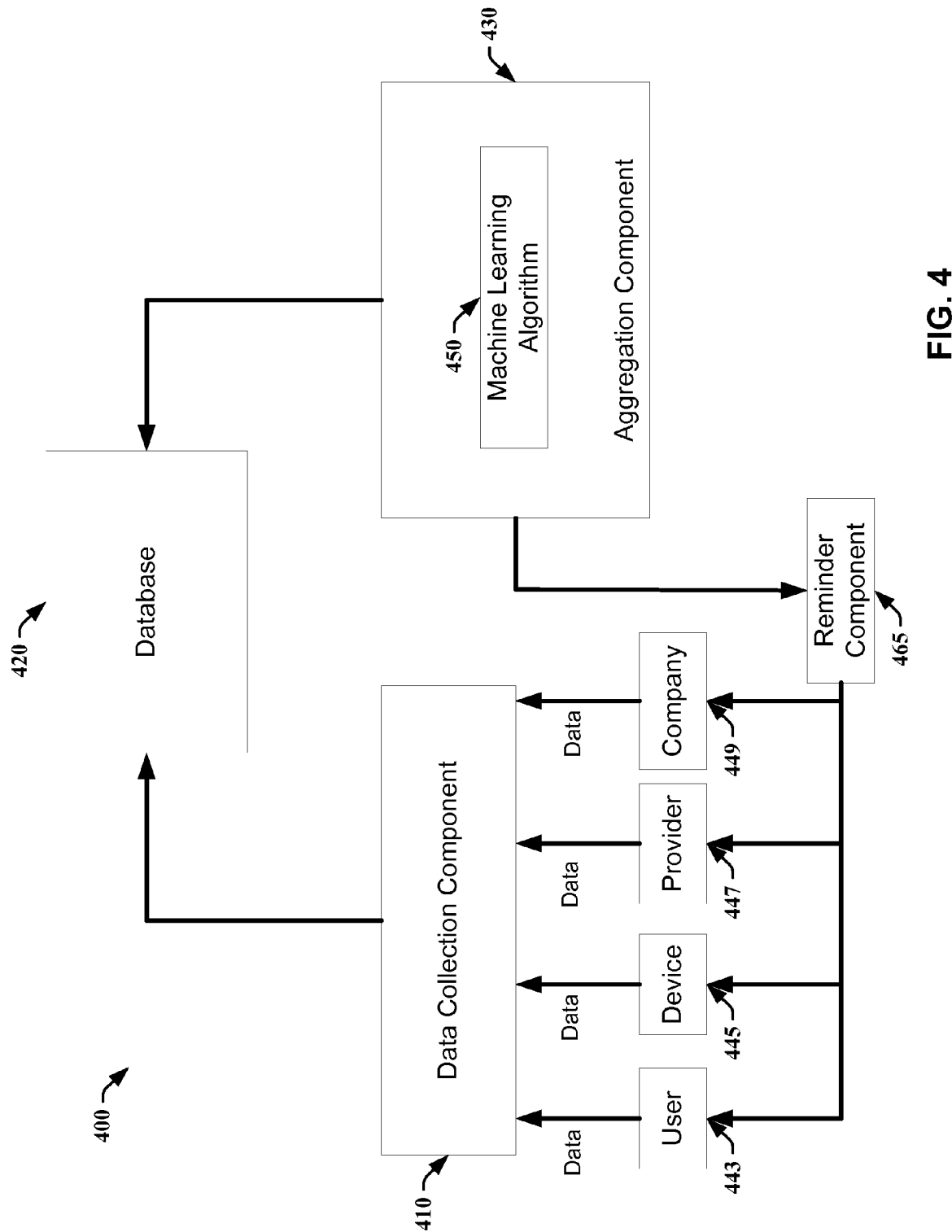
FIG. 4 is a block diagram of yet another example of a system that facilitates health-information reporting.

FIG. 4 schematically illustrates another example of a system 400 that facilitates large-scale reporting of health-related data. The system 400 comprises a data collection component 410, a database 420, an aggregation component 430 and a reminder component 365. The data collection component 410 collects data 440 on a large-scale from a non-selected population and provides the data 440 in whole or in part to the database 420. The aggregation component 430 applies a machine-learning algorithm 450 to the database 420 to discern patterns in the data 440. The reminder component 465 sends reminders to various entities 443-449. The reminder component 465 can send reminders in any form, including but not limited to a data signal, online transmission, wirelessly, email, telephone, facsimile, blackberry, cell phone, etc.

The components 410, 430 and 465 can be the same process executing on a single or a plurality of computers or multiple processes executing on a single or a plurality of computers. Similarly, the database 420 can be a single datastore or multiple datastores. Moreover, the components 410, 430 and 465 and the database 420 can be implemented by software or combinations of software and hardware.

The reminder component 465 can send reminders to remind various entities 443-449 to enter data. The reminders can be sent to any party/entity that requests to be reminded, such as users 443 (e.g., individuals, etc.), devices 445 (e.g., electronic calendars, consumer healthcare devices, pacemakers, etc.), providers 447 (e.g., physicians, nurses, hospitals, insurance companies, pharmacies, etc.) and companies 449 (e.g., pharmaceutical manufacturers, medical device manufacturers, distributors, etc.). Alternatively, the reminder component 465 can send out reminders automatically without receiving a request. For instance, the machine-learning component 450 can determine that information is missing from a profile and signal the reminder component 465 to send a request to the information source. Optionally, a fee can be charged for the reminder service. The reminder component 465 also can send alerts of the type described in relation to FIG. 3.

Figure 5:
FIG. 5 is an illustration of one example of an interface for reporting health-related information.
Figure 6:
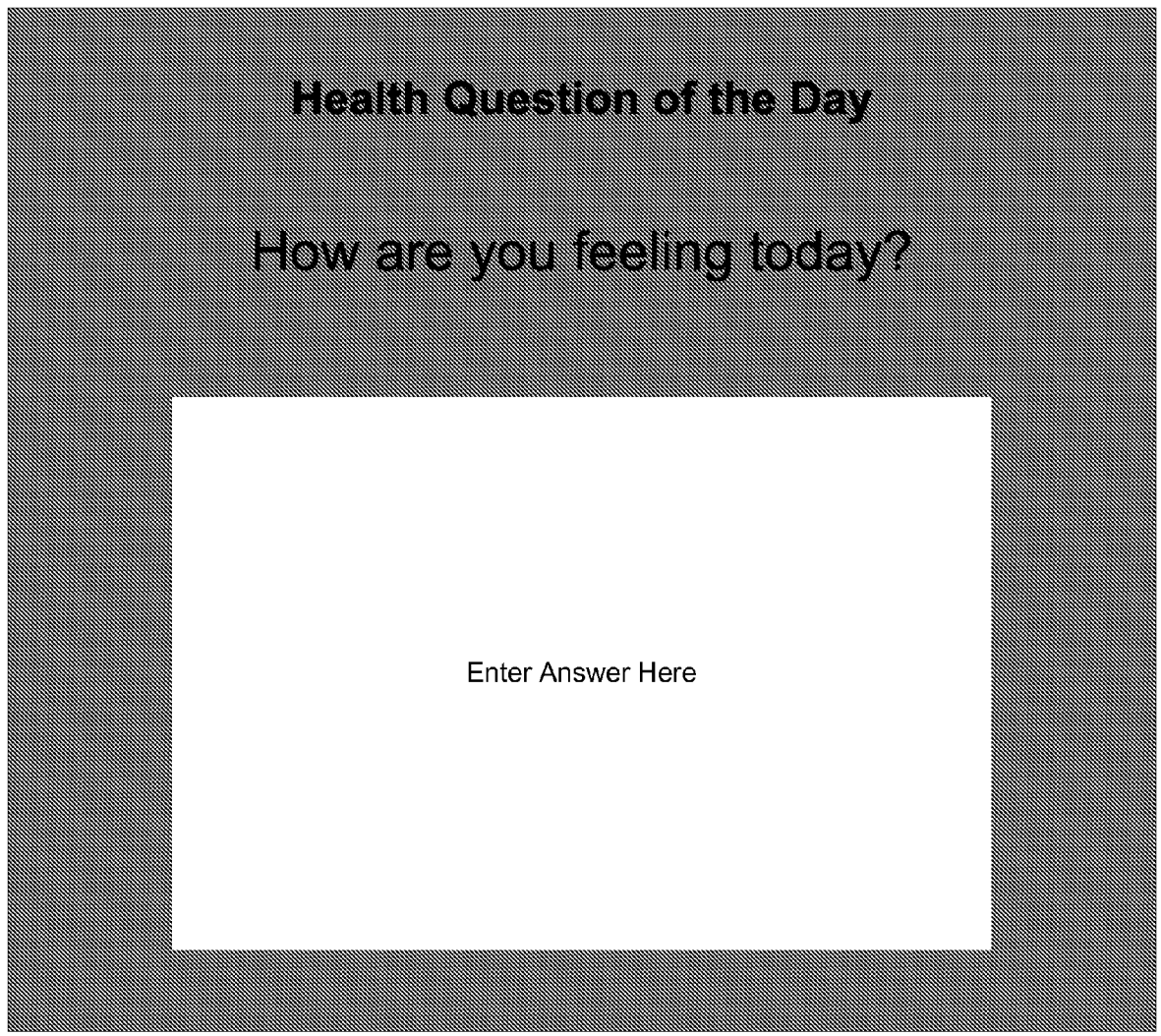
FIG. 6 is an illustration of another example of an interface for reporting health-related information.

FIGS. 5 and 6 are illustrations of two examples of an interface for reporting health-related information. FIG. 5 illustrates a survey form 500 provided to a user by a data collection component to obtain information about the user. FIG. 6 illustrates a free-text form 600 provided to a user by a data collection component to obtain information about the user. A user can enter the information in any format and the data collection component will extract structured information by employing, for instance, an artificial intelligence process.

The systems described above can be implemented on a network, in whole or in part, by data signals. These manufactured data signals can be of any type and can be conveyed on any type of network. For instance, the systems can be implemented by electronic signals propagating on electronic networks, such as the Internet. Wireless communications techniques and infrastructures also can be utilized to implement the systems.

Figure 7:
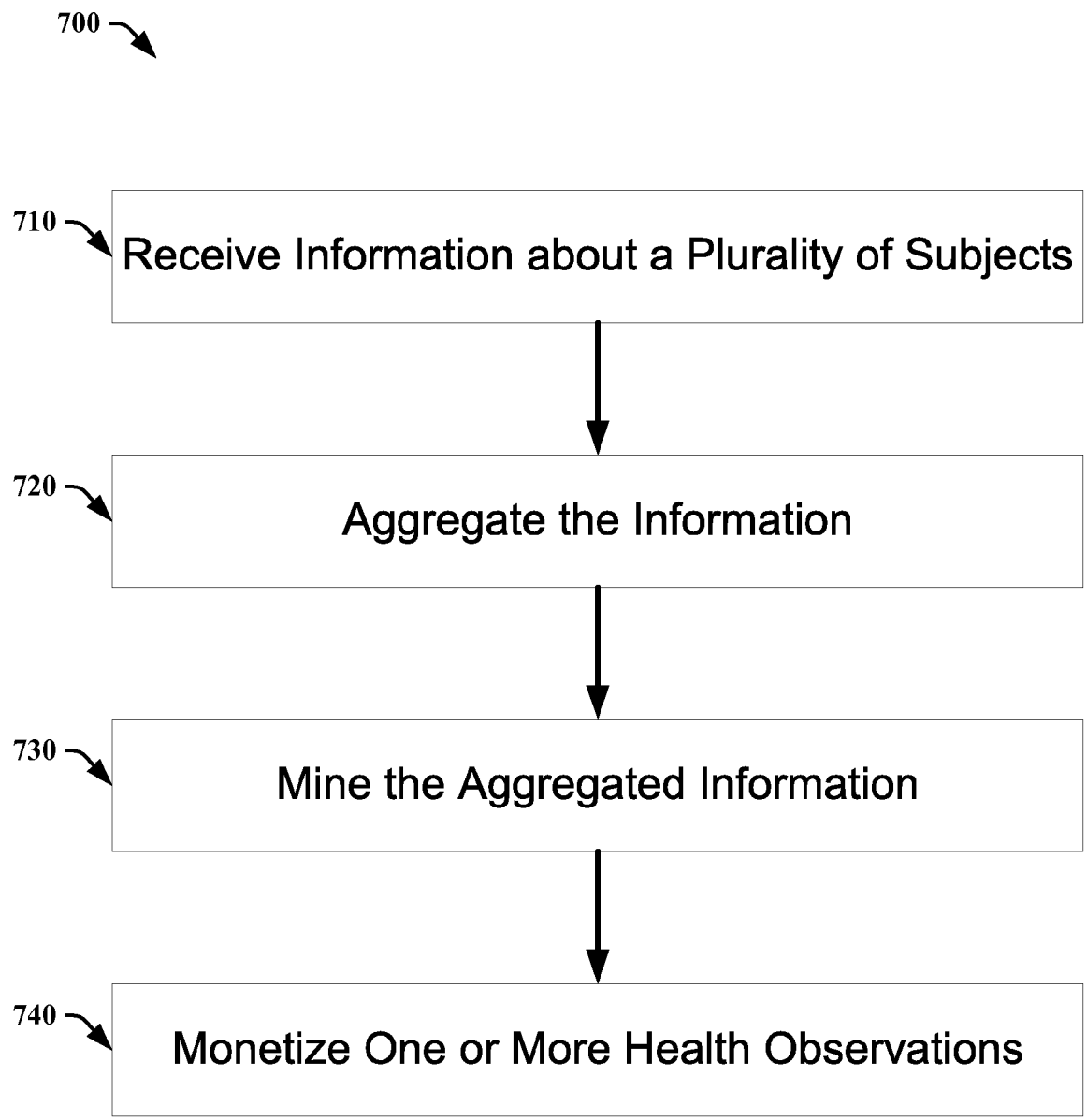
FIG. 7 is a flowchart representing one example of a method of extracting health observations.

FIG. 7 is a flowchart representing one example of a method 700 of extracting health observations from information obtained on a macro-scale. The method 700 can be implemented by computer-executable instructions stored on computer-readable media or conveyed by a data signal of any type. The method 700 can be implemented at least in part manually. The term macro-scale as used herein means on a scale sufficient to allow a machine-learning component to make reasonably valid inferences from aggregated data.

At step 710, information about a plurality of self-selected subjects is received. The information can be obtained from a consumer or a provider of healthcare services or any other source of information, such as a device or an electronic calendar. At step 720, the information is aggregated. At step 730, the aggregated data is mined. The aggregated information can be mined at least in part by employing a data-mining algorithm to infer one or more health observations from the aggregated information. The term health observation as used herein includes but is not limited to trends, associations, correlations, connections, links, relationships, etc. At step 740, the one or more health observations are monetized. Monetizing the health observations can be accomplished, for instance, by charging an interested party a fee for access to the health observations. The fee can be structured in any manner, for instance, a fee can be charged for each alert sent to a third party. Alternatively, a subscription service can be provided such that a third party is charged a fee for unlimited or limited access to health observations over a period of time. The method 700 can be repeated an unlimited number of times as needed to generate health observations.

Any type of information can be aggregated including but not limited to biological, pathophysiological, physiological, medical, healthcare and/or otherwise health-related. The information can be, for example, a drug-related event, a symptom, and/or genetic information. The data can be collected in any form including but not limited to textual, graphical, photographic, sound, speech, video, multimedia and the like. By way of example, the data can be collected by employing a free-text analysis, which optionally can include intelligent spelling correction or voice recognition. The data can be explicitly, implicitly and/or automatically input. The information can be entered by any input means, such as a PDA, telephone, bar code reader, computer, keyboard, mouse, microphone, touchscreen, database, cell phone, etc. Sources of information can be sent reminders either by request and/or inferred reminders.

In one embodiment, the information can be collected anonymously such that no identifying information is linked to the information. Alternatively, the data can be received in conjunction with identifying information and stripped of the identifying information by a privacy filter. Security measures can be employed in the information collection process, such as a Human Interactive Proof (HIP) to verify that a human being (rather than an automated process) is providing the data.

The health-observations (e.g., correlations) can be ascertained via any suitable method, for example, by employing the statistical methods explained above (Fisher's Exact Test, Mann-Whitney, Spearman correlation). Additionally or alternatively, the health-observations can be ascertained via an algorithm that uses low-order sufficient statistics and statistical methods that can make inferences with missing data (e.g., expectation-maximization (EM) algorithm). Other examples of data-mining methods include but are not limited to neural networks, expert systems, Bayesian belief networks, fuzzy logic, data fusion engines and the like as well as combinations of various artificial intelligence techniques capable of discerning patterns. Optionally, a human intervention step can be added to the process in order to mine the data. By way of example, a human editor can inspect and even test (e.g., through formal or informal clinical trials) some or all of the inferences provided by the data-mining algorithm.

In mining the aggregated data, information can be accorded different weights, for instance, information from a pharmacy can be given a higher weight than information from a patient. By way of another example, information more likely to be accurate can be assigned a greater weigh. By way of yet another example, the machine-learning algorithm can classify the information according to demographics (e.g., age, gender, race, etc.) in order to facilitate making demographic-specific health observations.

Figure 8:
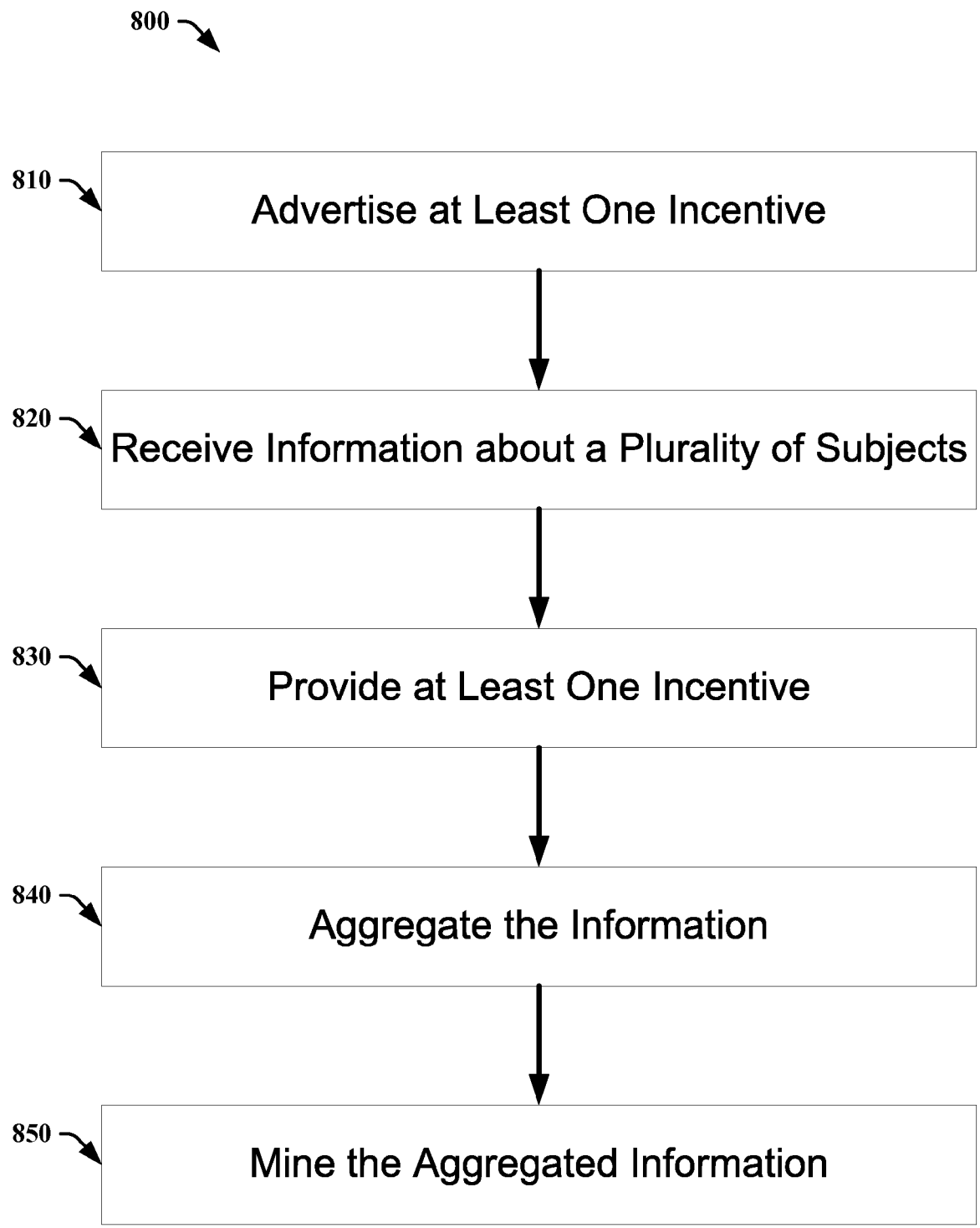
FIG. 8 is a flowchart representing another example of a method of extracting health observations.

FIG. 8 is a flowchart representing another example of a method 800 of extracting health observations from information obtained on a macro-scale. The method 800 can be implemented by computer-executable instructions stored on computer-readable media or conveyed by a data signal of any type. The method 800 can be implemented at least in part manually.

At step 810, at least one incentive to supply information is advertised. The incentive can be advertised, for example, on a search site upon entering a search string containing one or more keywords. Any other means of advertising can be used to advertise the incentive, such as print, TV, radio, online ad, etc. At step 820, information about a plurality of self-selected subjects is received. At step 830, the incentive is provided to the self-selected subject. The incentive can be of any type and can be a requirement or a bonus. For instance, an insurance company (e.g., Medicare, Medicaid, private insurer, etc.) can require a subscriber to file a report as a condition of renewing a prescription for medication or to qualify for a lower co-payment/rate. By way of another example, coupons for discounts on goods and services can be offered. At step 840, the information is aggregated. At step 850, the aggregated data is mined. The aggregated information can be mined at least in part by employing a data-mining algorithm to infer one or more health observations from the aggregated information. The method 800 can be repeated an unlimited number of times as needed to generate health observations. Moreover, the method 800 is not limited to the order shown in the flowchart. For instance, step 830 can be performed prior to step 820.

As described in relation to FIG. 7 above, the information can be entered anonymously or stripped of identifying information. The information can be obtained from a consumer or a provider of healthcare services or any other source of information, such as a device or an electronic calendar, can be in any form and can be provided by any input means. The data-mining algorithm also can be of any type.

Figure 9:
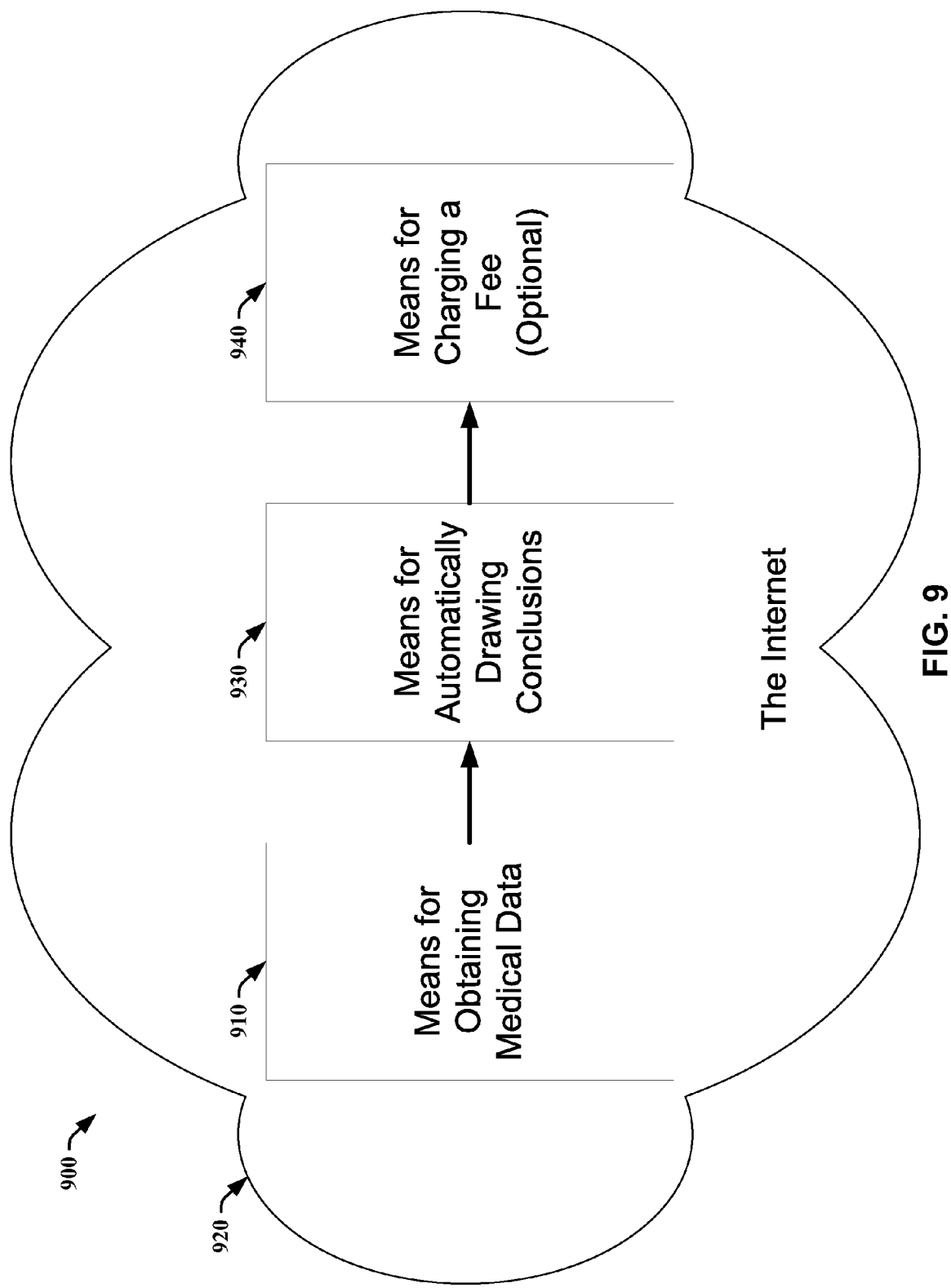
FIG. 9 is a block diagram of one example of a system to facilitate large-scale medical data analysis.

FIG. 9 is a block diagram of one example of an online system 900 to facilitate global medical data analysis. The term global as applied to the online system 900 and used herein means an online system capable of reaching a geographically, wide-spread population. The system 900 includes means for obtaining medical data from a global, unselected population 910 via the Internet 920 and means for automatically drawing conclusions from the medical data 930. The means for automatically drawing conclusions from the medical data 930 can employ one or more artificial intelligence algorithms to draw at least one conclusion from the medical data. Optionally, the system 900 can include a means for charging a fee 940. In one embodiment, the fee can be charged to receive the conclusions drawn by the artificial intelligence algorithms. In another embodiment, the fee can be assessed to gain access to the system 900.

The structures and algorithms described in relations to FIGS. 1-8 above can be used to implement the means 910, 930 and 940 of the system 900. As described in relation to FIGS. 1-8, the data can be entered anonymously or stripped of identifying information. The information can be obtained from a consumer or a provider of healthcare services or any other source of information, such as a device or an electronic calendar, can be in any form and can be provided by any input means. The data-mining algorithm also can be of any type.

Figure 10:
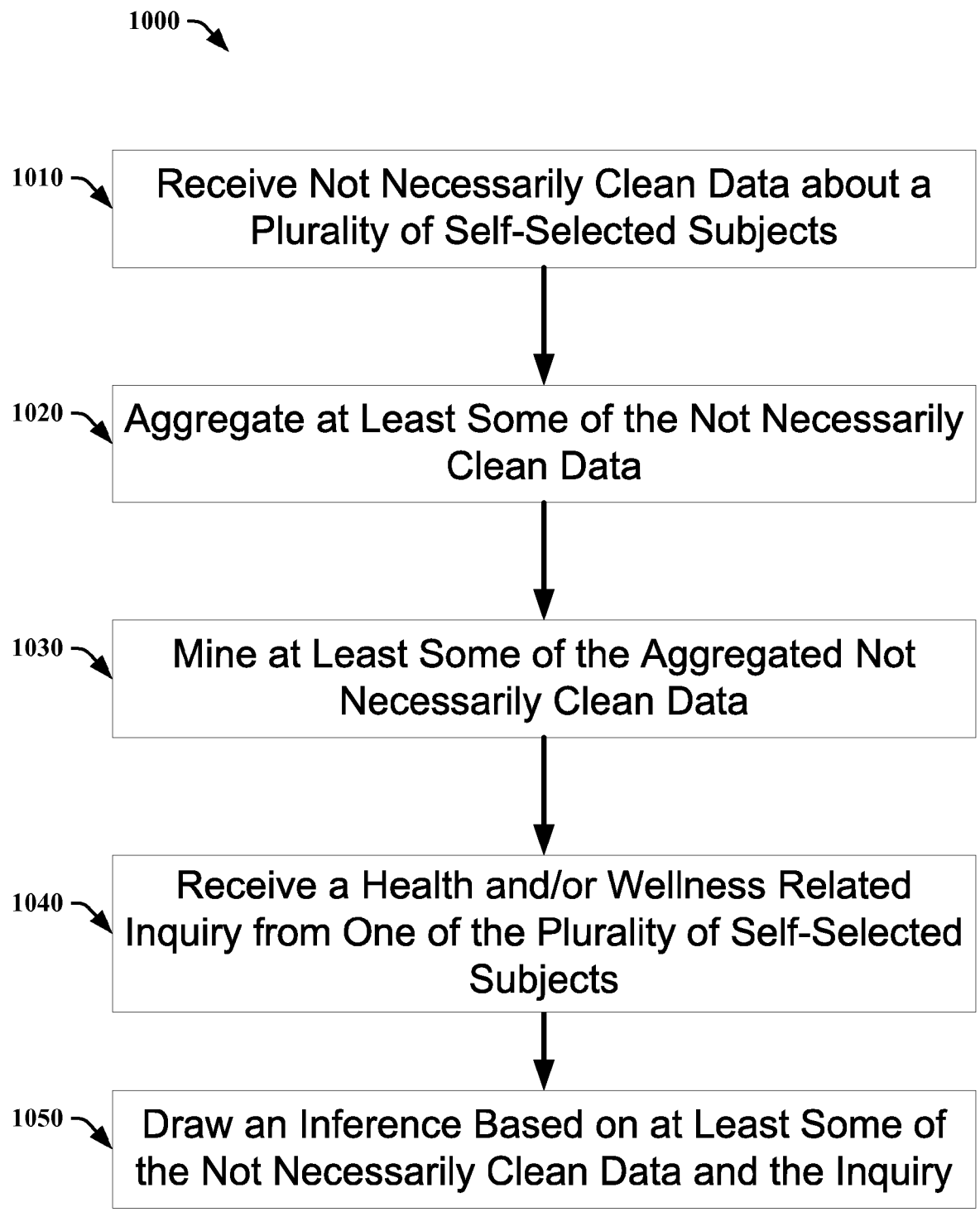
FIG. 10 is a flowchart representing one example of a method of providing health and/or wellness services

A database of data gathered as described in relation to FIGS. 1-9 can be further used to facilitate providing health and/or wellness advice/services to a user as will be described in relation to FIGS. 10-17. FIG. 10 is a flowchart of one example of a method 1000 of providing health and/or wellness services. At step 1010, not necessarily clean data about a plurality of self-selected subjects is received and at 1020, at least some of the data is aggregated. Examples of the type of data include but are not limited to those described in relation to FIG. 1. The aggregated data is mined at step 1030 at least in part by employing, for instance, one or more of a statistical algorithm, a data-mining algorithm and a machine-learning algorithm. At step 1040, a health and/or wellness related inquiry from one of the plurality of self-selected subjects is received. An inference about the health and/or wellness of the one of the plurality of self-selected subjects is drawn at step 1050. The inference can be based on, for instance, at least some of the data about the one of the plurality of self-selected subjects and the health and/or wellness inquiry. Examples of an inference that can be drawn include a diagnosis, a treatment option (e.g., over-the-counter medication recommendation, alternative medicine regiments, recommendation to seek emergency treatment, etc.) or other health/wellness advice such as information on diet, exercise or other activities, and/or appropriate nutritional supplements. The inference can be drawn using any suitable technique, such as neural networks, expert systems, Bayesian belief networks, fuzzy logic, data fusion engines and the like as well as combinations thereof Moreover, a human intervention step can be combined with these techniques to draw the inference.

Figure 11:
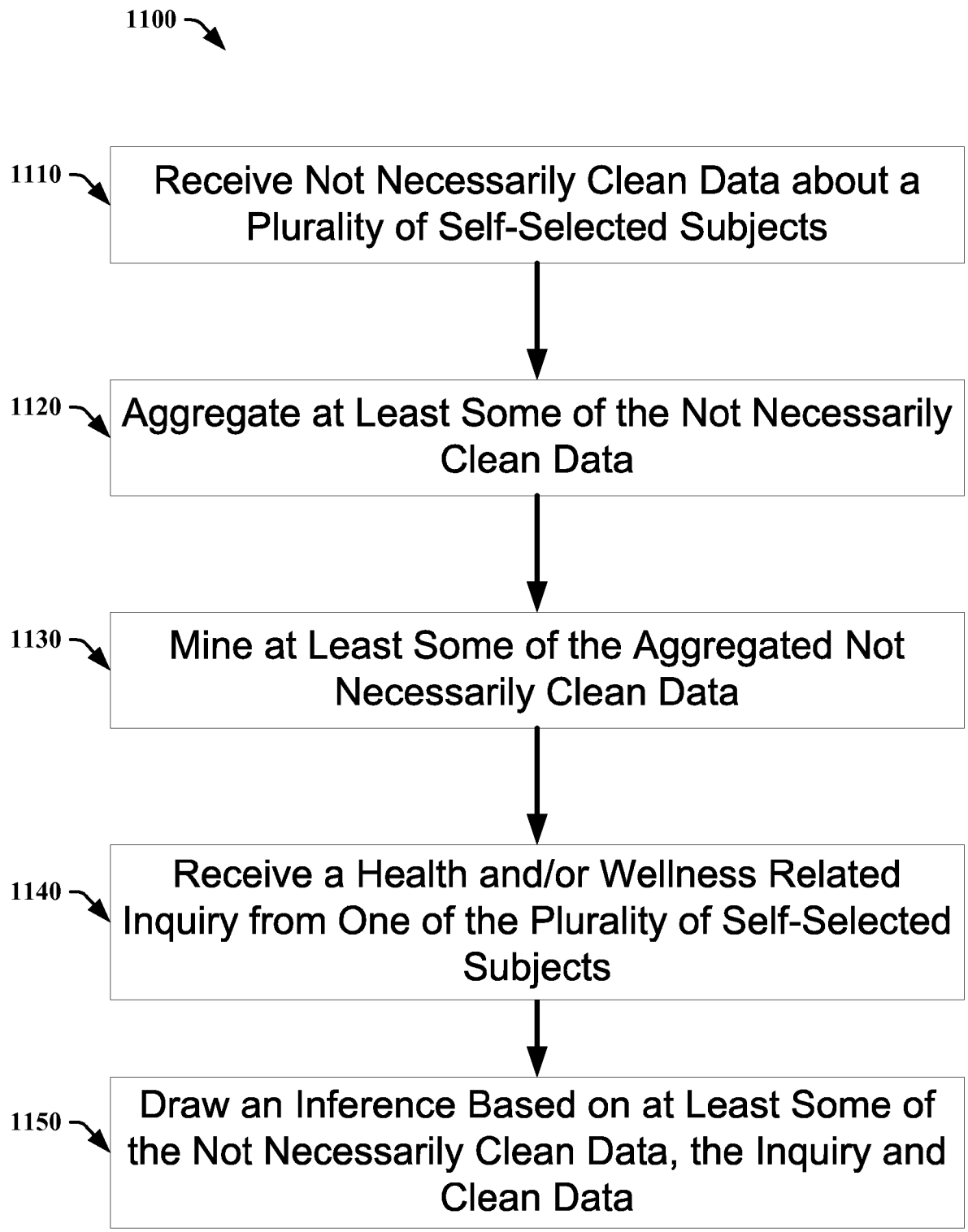
FIG. 11 is a flowchart representing another example of a method of providing health and/or wellness services.
Figure 12:
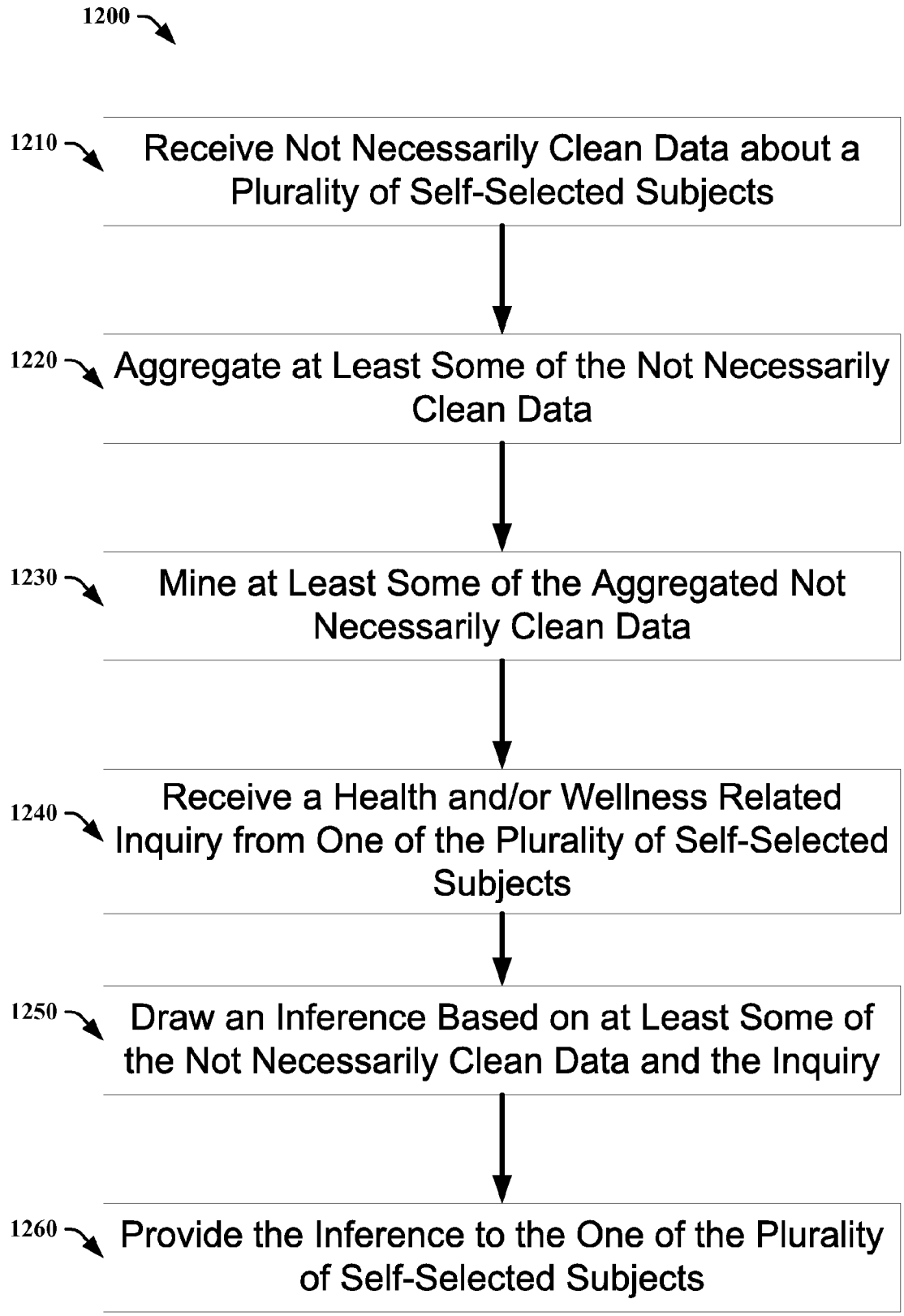
FIG. 12 is a flowchart representing another example of a method of providing health and/or wellness services.
Figure 13:
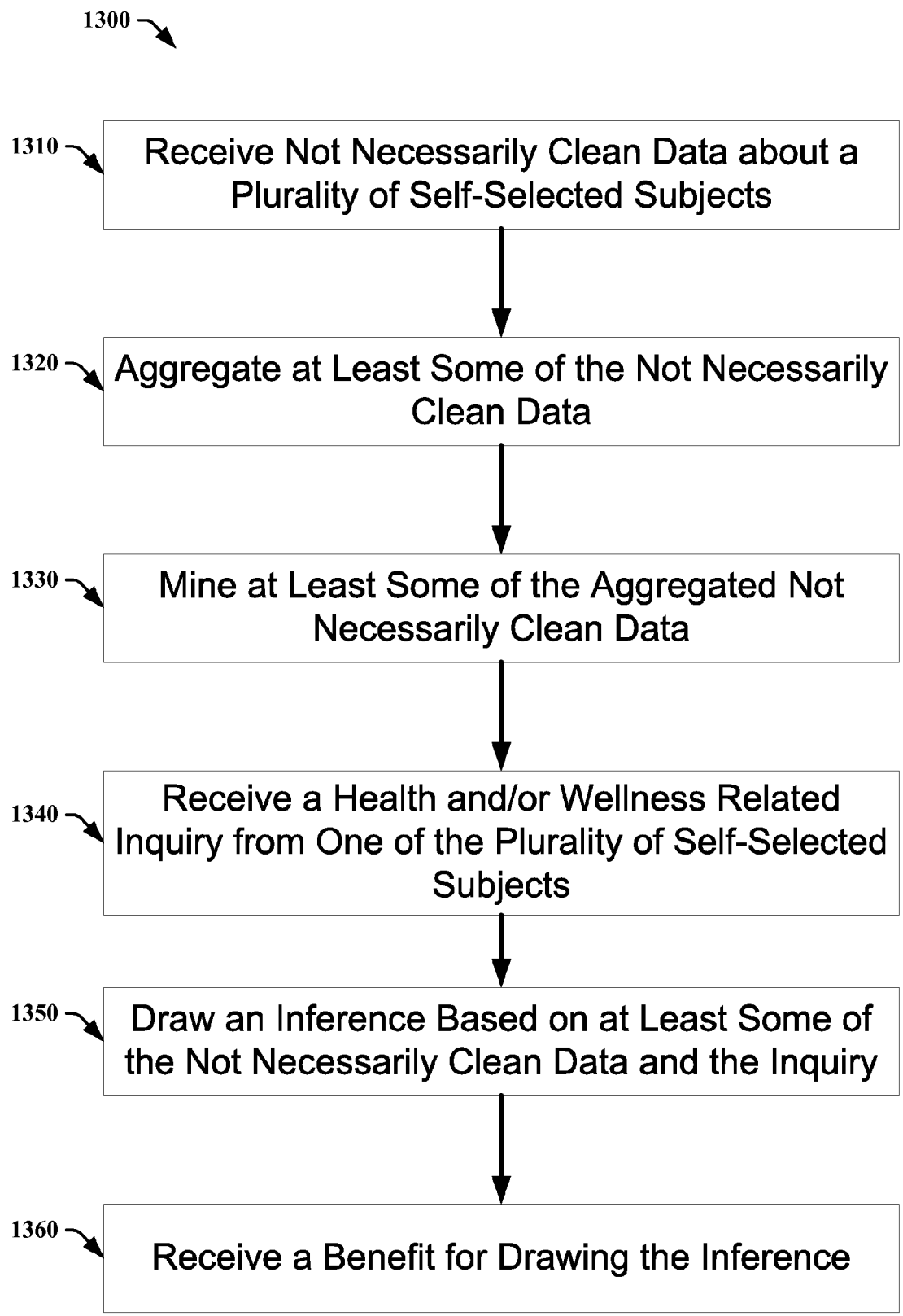
FIG. 13 is a flowchart representing another example of a method of providing health and/or wellness services.
Figure 14:
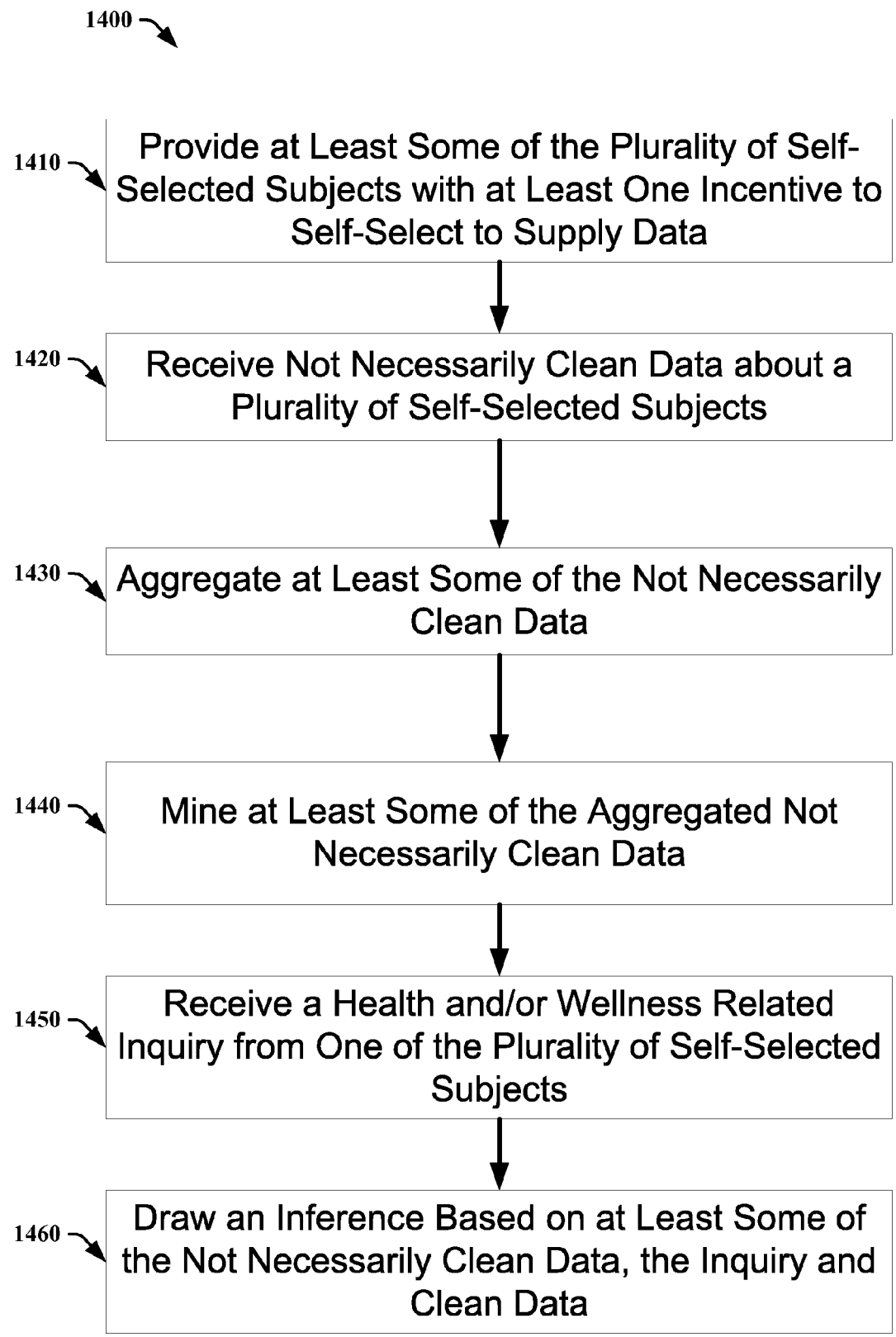
FIG. 14 is a flowchart representing another example of a method of providing health and/or wellness services.
Figure 15:
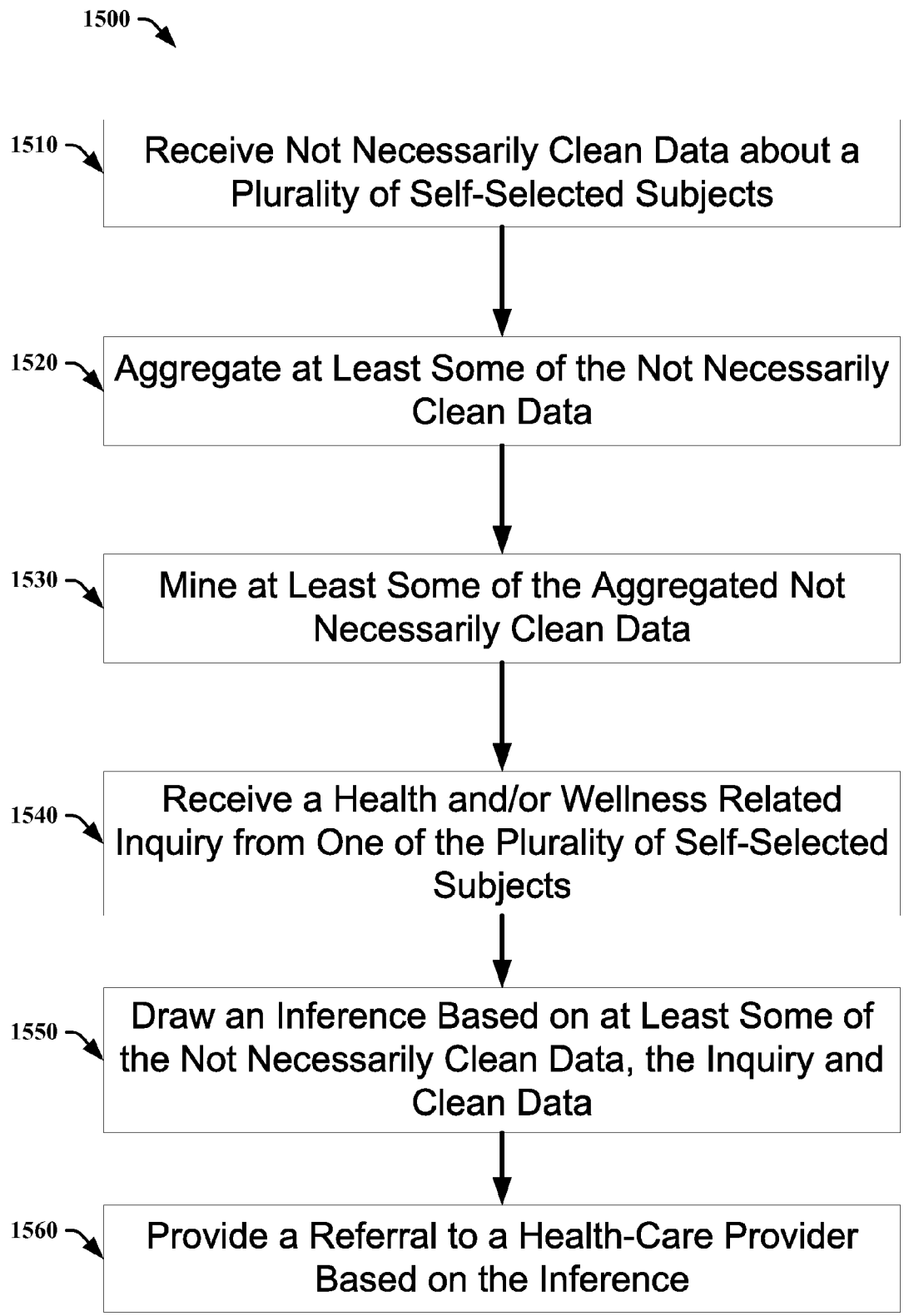
FIG. 15 is a flowchart representing yet another example of a method of providing health and/or wellness services.

As shown in FIG. 11, the inference can be further based at least in part on clean data 1150. Examples of clean data include a randomized clinical trial, a controlled clinical trial, a double-blind clinical trial, a double-blind, randomized, controlled clinical trial or a meta-analysis of two or more clinical trials. As shown in FIG. 12, the inference can be provided to the inquirer 1260. As shown in FIG. 13, a benefit can be received for drawing the inference about health and/or wellness of the inquirer 1360. Examples of a benefit include a monetary benefit such as advertising revenue received in return for displaying advertisements to the inquirer, a fee paid by the inquirer to receive health/wellness advice and/or a referral fee paid by a heath-care entity for referring the inquirer for medical services. As shown in FIG. 14, at least some of the plurality of self-selected subjects can be provided with one or more incentives to self-select to supply the data. Incentives include but are not limited to those described in relation to FIG. 8. As shown in FIG. 15, a referral to a healthcare provider can be provided to the inquirer based on the inference 1560. Referrals include but are not limited to providing the inquirer with a name and/or contact information or facilitating making an appointment with a health-care provider for the inquirer (e.g., automated appointment).

Figure 16:
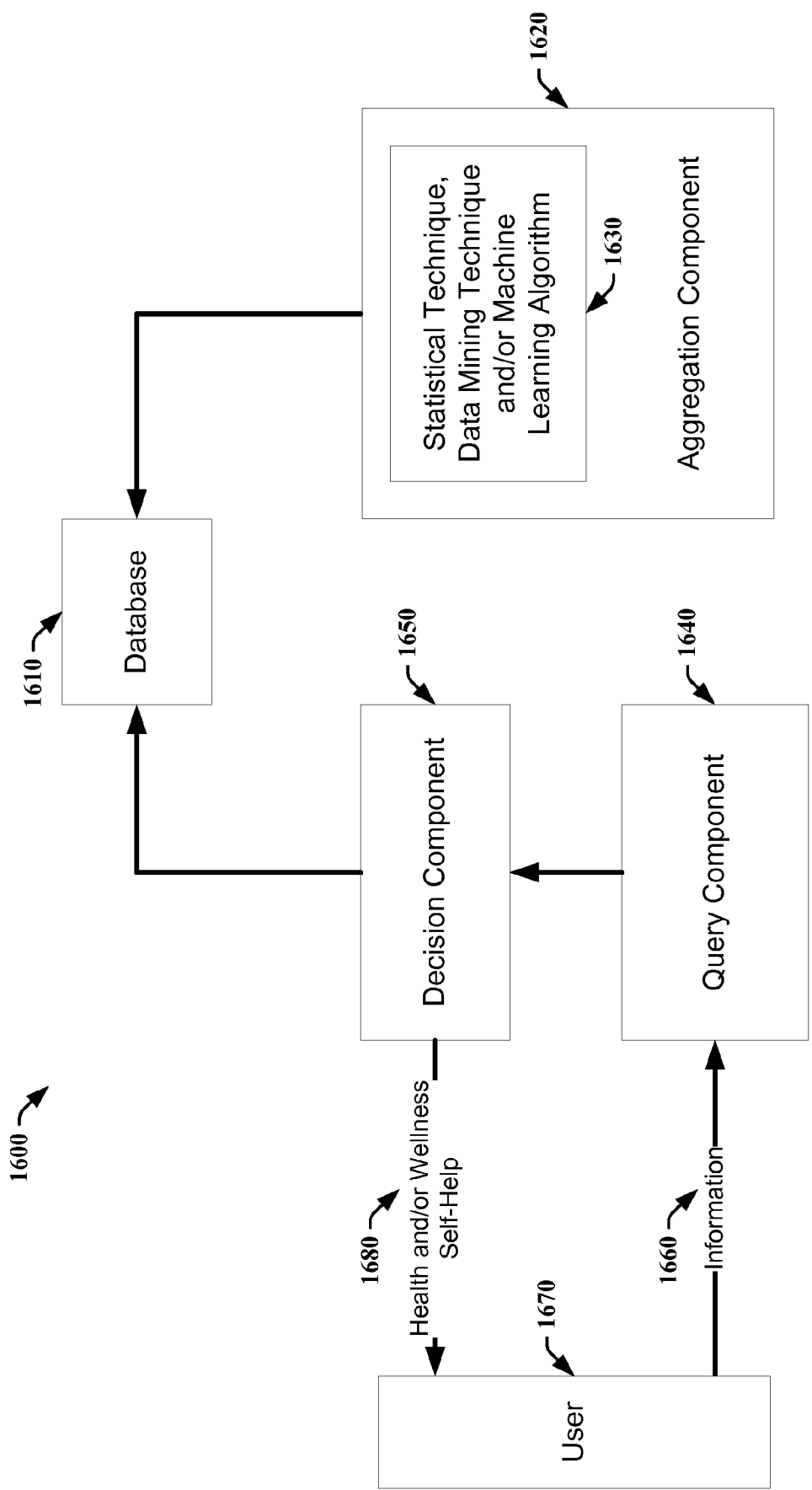
FIG. 16 is a block diagram representing one example of a system that facilitates providing health and/or wellness services.

FIG. 16 is a block diagram of one example of a system 1600 that facilitates providing health and/or wellness services. The system 1600 can be implemented on a single server or in a distributed environment, for instance, on two or more servers. The system 1600 includes a database 1610 to store unclean health-related data gathered on a large-scale and relating to a non-selected population. An aggregation component 1620 facilitates automatically ascertaining at least one pattern from the unclean health-related data, for instance by applying statistical techniques, data mining techniques and/or machine-learning techniques 1630 to the database. More detailed examples of this are described in relation to FIGS. 1-9. The system 1600 also includes a query component 1640 and a decision component 1650. The query component 1640 receives information 1660 from a user 1670 (e.g. one of the non-selected population) and the decision component 1650 employs the information 1660 received from the user and at least some of the unclean health-related data relating to the user stored in the database 1610 to provide health and/or wellness self-help 1680 to the user 1670.

The information 1660 received from the user can be a drug-related event, a symptom, a device output, an activity, and/or patient-specific genetic information or any other type of information 1660 that would facilitate providing health and/or wellness services. The decision component 1650 can employ various techniques 1630 to arrive at a conclusion for instance, neural networks, expert systems, Bayesian belief networks, fuzzy logic, data fusion engines and the like as well as combinations thereof. Moreover, a human intervention step can be combined with the techniques 1630 to arrive at a conclusion.

The query component 1640 can implicitly collect data from the user, for instance, as is described in relation to FIGS. 1-9 (e.g., based on the user's context, etc.). The query component 1640 can automatically collect at least some of the information received from the user, for instance, by automatically querying a device (e.g., smart scale, cardiac pacemaker, glucose meter, pedometer, etc.). The query component 1640 can collect at least some of the information received from the user by prompting the user with at least one question and/or determining one or more follow-up questions as described in relation to FIG. 2.

The unclean health-related data can be provided by entities interfacing with the system 1600 via an Application Programming Interface (e.g., MICROSOFT .NET). By way of example, an Application Programming Interfaces (API) for the transfer of health context information using web services is provided. The API provides a framework for software developers to develop applications that allow entities to seamlessly transfer health context information and that facilitates a distributed framework of commerce focused around health context information. For instance, a first party can generate diagnostic tools, another party can provide treatment tools, another provide billing services, another advertisements, informatics tools, insurance, marketing, etc. all using common data to provide customized products and services that can be seamlessly aggregated to provide a range of services to users.

As used in this application, the term "component" is intended to refer to a computer-related entity, either hardware, a combination of hardware and software, software, or software in execution. For example, a component can be, but is not limited to, a process running on a processor, a processor, an object, an executable, a thread of execution, a program, and a computer. By way of illustration, an application running on a server and/or the server can be a component. In addition, a component can include one or more subcomponents. One or more components can reside within a process and/or thread of execution and a component can be localized on one computer and/or distributed between two or more computers.

FIG. 17 is a block diagram of one example of an online system 1700 to facilitate providing health and/or wellness assistance. The system 1700 includes a means for obtaining unclean medical data 1710 from an unselected population via the Internet 1720. The unclean medical data is used by the means for automatically drawing conclusions 1730 to draw conclusions. The means for automatically drawing conclusions 1730 can employ, for instance, one or more of a statistical algorithm, a machine-learning algorithm, a data-mining algorithm and an artificial-intelligence algorithm to draw conclusions. The system 1700 also includes a means for receiving a query 1740 from a member of the unselected population and a means for providing the member with a conclusion 1750. The conclusion can be based on, for instance, at least the query and at least some of the medical data relating to the member. The means 1710, 1730, 1740 and 1750 of the system 1700 include but are not limited to the structures and algorithms described in relation to FIGS. 1-16 above.

As used in this application, the term "means" is intended to refer to a computer-related entity, either hardware, a combination of hardware and software, software, or software in execution. For example, a means can be, but is not limited to being, a process running on a processor, a processor, an object, an executable, a thread of execution, a program, and/or a computer. By way of illustration, both an application running on a server and the server can be a means. One or more means can reside within a process and/or thread of execution and a means can be localized on one computer and/or distributed between two or more computers. A thread is the entity within a process that the operating system kernel schedules for execution. As is well known in the art, each thread has an associated context which is the volatile data associated with the execution of the thread. A thread's context includes the contents of system registers and the virtual address belonging to the thread's process. Thus, the actual data comprising a thread's context varies as it executes.

The subject matter described herein can operate in the general context of computer-executable instructions, such as program modules, executed by one or more components. Generally, program modules include routines, programs, objects, data structures, etc., that perform particular tasks or implement particular abstract data types. Typically, the functionality of the program modules can be combined or distributed as desired. Although the description above relates generally to computer-executable instructions of a computer program that runs on a computer and/or computers, the user interfaces, methods and systems also can be implemented in combination with other program modules. Generally, program modules include routines, programs, components, data structures, etc. that perform particular tasks and/or implement particular abstract data types.

Moreover, the user interfaces, methods and systems described herein can be practiced with all computer system configurations, including single-processor or multiprocessor computer systems, mini-computing devices, mainframe computers, personal computers, stand-alone computers, hand-held computing devices, wearable computing devices, microprocessor-based or programmable consumer electronics, and the like as well as distributed computing environments in which tasks are performed by remote processing devices that are linked through a communications network. In a distributed computing environment, program modules can be located in both local and remote memory storage devices. The user interfaces, methods and systems described herein can be embodied on a computer-readable medium having computer-executable instructions as well as signals (e.g., electronic signals) manufactured to transmit such information, for instance, on a network.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

It is, of course, not possible to describe every conceivable combination of components or methodologies that fall within the claimed subject matter, and many further combinations and permutations of the subject matter are possible. While a particular feature may have been disclosed with respect to only one of several implementations, such feature can be combined with one or more other features of the other implementations of the subject matter as may be desired and advantageous for any given or particular application.

In regard to the various functions performed by the above described components, computer-executable instructions, means, systems and the like, the terms are intended to correspond, unless otherwise indicated, to any functional equivalents even though the functional equivalents are not structurally equivalent to the disclosed structures. Furthermore, to the extent that the terms "includes," and "including" and variants thereof are used in either the specification or the claims, these terms are intended to be inclusive in a manner similar to the term "comprising." Accordingly, the claimed subject matter is intended to embrace all such alterations, modifications, and variations that fall within the spirit and scope of the appended claims.

What is claimed is:

1. An online system to facilitate providing health and/or wellness assistance, comprising:
    means for obtaining unclean medical data from an unselected population via the Internet;
    means for automatically drawing conclusions from the unclean medical data, the means for automatically drawing conclusions from the unclean medical data employing a statistical algorithm, a machine-learning algorithm, a data-mining algorithm and/or an artificial-intelligence algorithm to draw at least one conclusion from the unclean medical data;
    means for receiving a query from a member of the unselected population; and
    means for providing the member of the unselected population with a conclusion based on at least the query and at least some of the unclean medical data relating to the member of the unselected population.

2. The online system of claim 1, wherein the means for providing the member of the unselected population with a conclusion are further based at least in part on clean data from at least one of: a randomized clinical trial, a controlled clinical trial, a double-blind clinical trial, a double-blind, randomized, controlled clinical trial, or a meta-analysis of two or more clinical trials.

3. The online system of claim 1, further comprising means for receiving a benefit for providing the conclusion to the member of the unselected population.

4. The online system of claim 1, wherein the unclean medical data is provided by entities interfacing with the online system via an Application Programming Interface.

5. A method of providing health and/or wellness assistance, comprising:
    obtaining unclean medical data from an unselected population via the Internet;
    automatically drawing conclusions from the unclean medical data, by employing at least one of: a statistical algorithm, a machine-learning algorithm, a data-mining algorithm, or an artificial-intelligence algorithm to draw at least one conclusion from the unclean medical data;
    receiving a query from a member of the unselected population; and
    providing the member of the unselected population with a conclusion based on at least the query and at least some of the unclean medical data relating to the member of the unselected population.

6. The method of claim 5, wherein the conclusion is further based at least in part on clean data from at least one of: a randomized clinical trial, a controlled clinical trial, a double-blind clinical trial, a double-blind, randomized, controlled clinical trial, or a meta-analysis of two or more clinical trials.

7. The method of claim 5, further comprising receiving a benefit for providing the conclusion to the member of the unselected population.

8. The method of claim 7, wherein the benefit is a monetary benefit.

9. The method of claim 5, further comprising providing at least some members of the unselected population with at least one incentive to self-select to supply the unclean medical data.

10. The method of claim 9, further comprising providing a referral to a health-care provider based on the conclusion.

11. The method of claim 5, wherein the conclusion comprises at least one of a diagnosis or a treatment option.

12. A computer readable media storing computer-executable instructions that, when executed on a processor, perform acts to facilitate providing health and/or wellness assistance, the acts comprising:
    obtaining unclean medical data from an unselected population via the Internet;
    automatically drawing conclusions from the unclean medical data, by employing at least one of: a statistical algorithm, a machine-learning algorithm, a data-mining algorithm, or an artificial-intelligence algorithm to draw at least one conclusion from the unclean medical data;
    receiving a query from a member of the unselected population; and
    providing the member of the unselected population with a conclusion based on at least the query and at least some of the unclean medical data relating to the member of the unselected population.

13. The computer readable media of claim 12, wherein the conclusion is further based at least in part on clean data.

14. The computer readable media of claim 12, the acts further comprising receiving a benefit for providing the conclusion to the member of the unselected population.

* * * * *